United States Patent [19]

Usui et al.

[11] Patent Number: 4,725,407
[45] Date of Patent: Feb. 16, 1988

[54] FLOW THROUGH TYPE LIQUID ANALYZER

[75] Inventors: Seiji Usui; Hiroaki Takahasi; Kunio Terada, all of Kyoto, Japan

[73] Assignee: Horiba, Ltd., Kyoto, Japan

[21] Appl. No.: 841,456

[22] Filed: Mar. 19, 1986

[30] Foreign Application Priority Data

Apr. 29, 1985 [JP] Japan .................................. 60-63716

[51] Int. Cl.⁴ ............................................ G01N 35/08
[52] U.S. Cl. ........................................ 422/82; 436/53
[58] Field of Search ...................... 436/52, 53; 422/81, 422/82

[56] References Cited

U.S. PATENT DOCUMENTS

| | | | |
|---|---|---|---|
| 3,871,826 | 3/1975 | Bakay | 436/53 |
| 3,912,452 | 10/1975 | Sodickson et al. | 422/81 |
| 4,219,530 | 8/1980 | Kopp et al. | 422/81 |
| 4,399,362 | 8/1983 | Cormier et al. | 422/82 |
| 4,517,302 | 5/1985 | Saros | 436/180 |

Primary Examiner—Michael S. Marcus

Attorney, Agent, or Firm—Wenderoth, Lind & Ponack

[57] ABSTRACT

A flow through type liquid analyzer has
an analytical portion;
a peristaltic pump connected to the analytical portion for supplying various kinds of liquids to the analytical portion, a passage-change over valve mechanism for controlling the kinds of liquid supplied to the analytical portion,
an air bubble adding mechanism for adding air bubbles to the liquid sent to the analytical portion from the passage-change over valve mechanism,
a detecting device for detecting movement of the air bubbles from the air bubble adding mechanism to the analytical portion, and a controller connected to the detecting device and to the pump for determining the flow rate of the liquid being sent to the analytical portion from the detected movement and controlling the speed of rotation of the pump in response to the determined flow rate for automatically maintaining the flow rate of the liquid sent to the analytical portion at a predetermined desired value.

4 Claims, 5 Drawing Figures

FLOW THROUGH TYPE LIQUID ANALYZER

BACKGROUND OF THE INVENTION

1. Field of the Invention

The present invention relates to a flow through type liquid analyzer, in particular a flow through type liquid analyzer provided with a passage-change over valve mechanism for selectively supplying an analytical portion of the analyzer with various kinds of liquid supplied through a peristaltic pump and a bubble-adding mechanism for adding bubbles to the liquid sent to said analytical portion from said passage-change over mechanism.

2. Description of the Prior Art

In a liquid analyzer of this type, since it is important to supply an analytical portion of the analyzer with a sample liquid or various kinds of liquid to be measured little by little, a peristaltic pump (called also a tubing pump) has been used for the liquid-supplying means, as above described. Also, since various hindrance to the measurements, such as a disturbance of the liquid in the analytical portion, a change in the property and state of the liquids and the interference of liquids with each other, have occurred when various kinds of liquid are continuously introduced into said analytical portion, it has been the practice to use an air bubble-adding mechanism for adding air bubbles to a liquid sent to said analytical portion from a passage-change over valve mechanism when the passages of said passage-change over valve mechanism are changed over for selectively supplying the analytical portion with various kinds of liquid sent by said peristaltic pump. Close attention has been paid to the control of the frequency of rotation of said peristaltic pump to keep it at a constant value, and to highly accurate maintenance of the standards, such as the inside diameter, the outside diameter and elastic modulus, of the liquid-supplying tube used in the peristaltic pump at the appointed values in order to control the quantity of the liquid supplied to said analytical portion with high accuracy.

However, since the quantity of the liquid supplied to said analytical portion is very small, the slightest manufacturing error in the liquid-supplying tube used in said peristaltic pump, which is the liquid-supplying means, has an unnegligibly great influence upon the quantity of the liquid supplied to said analytical portion. Accordingly, not only is it very difficult to obtain liquid analyzers having identical standards to a problem-free extent, but also much waste is apt to be produced. Also, since the characteristics of the liquid-supplying tube are apt to change due to a deterioration in elasticity and a change in shape during the use thereof, the quantity of the liquid supplied by the peristaltic pump changes rather significantly with the passage of time. In addition, since such change in the quantity of liquid supplied by the peristaltic pump due to the change in the tube characteristics is very significant immediately after the start of use of the tube, this problem cannot be eliminated by simply replacing the tube. Moreover, this problem becomes a particularly big hindrance in the event that the quantity of liquid supplied is changed, i.e. the rate of operation of the pump is changed.

SUMMARY OF THE INVENTION

The present invention has been made to overcome these problems and has as its object to provide a flow-through type liquid analyzer wherein the quantity of liquid supplied to the analytical portion of the analyzer can always be maintained at a set value with high accuracy and for a long time even though a slight manufacturing error exists in the liquid-supply tube used in the peristaltic pump or the properties and characteristics of the liquid-supply tube change with the passage of time.

BRIEF DESCRIPTION OF THE DRAWING

This object is achieved by an analyzer as described hereinafter in connection with the drawings, in which.

DETAILED DESCRIPTION

Figure 1:
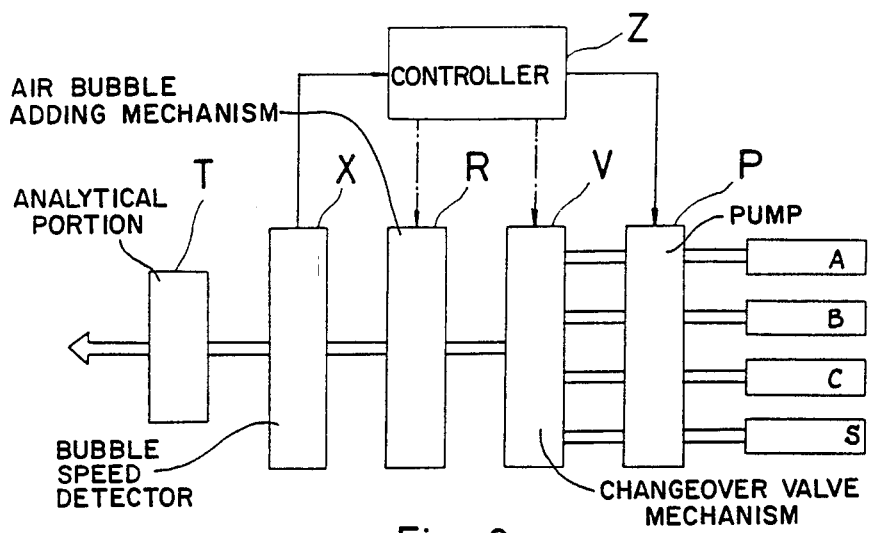
FIG. 1 is a basic block diagram of a flow-through type liquid analyzer according to the present invention.
Figure 2:
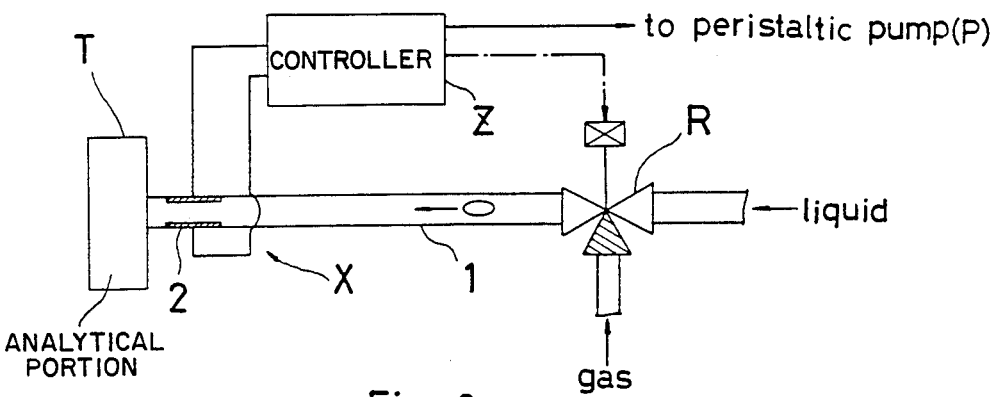
FIGS. 2 and 3 are general block diagrams showing an embodiment of principal parts of the analyzer of FIG. 1, respectively.
Figure 3:
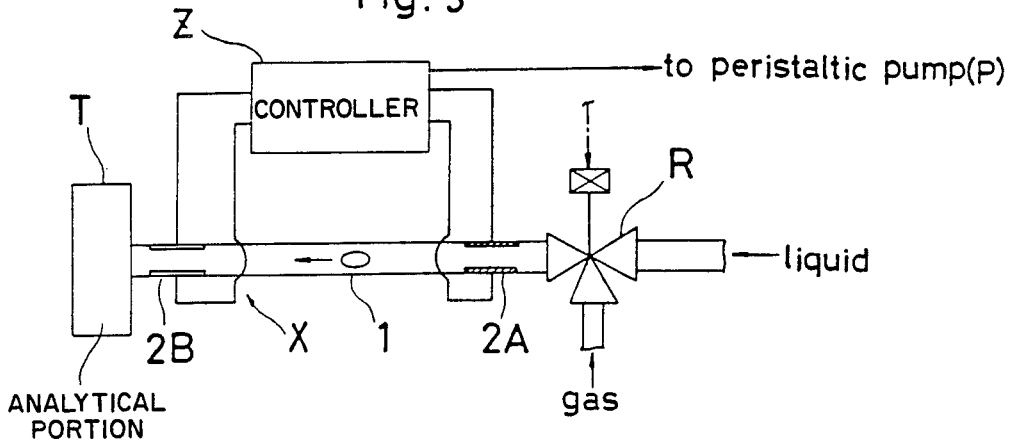

Referring to FIGS. 1-3, the flow-through type liquid analyzer of the present invention comprises a passage-change over valve mechanism V for selectively supplying an analytical portion T of the analyzer with various kinds of liquids A, B, C and S supplied through a peristaltic pump P and an air bubble-adding mechanism R for adding air bubbles to a liquid sent to said analytical portion T from said passage-change over valve mechanism V. The analyzer is characterized in that there are provided means X for detecting the speed of movement of air bubbles sent to said analytical portion T from said air bubble-adding mechanism R and a controller Z for automatically maintaining the flow rate of the liquid sent to said analytical portion T at a set value by controlling the frequency of rotation of said peristaltic pump P on the basis of the detected result of the speed of movement of the air bubbles by said means X.

The effects due to such a construction are as follows:

With a flow-through type liquid analyzer of the present invention, a change in the velocity of flow of the liquid sent to the analytical portion T and consequently a change in the quantity is detected by effectively utilizing the air bubbles which exist within the liquid in a liquid analyzer of this type. A change in the speed of movement of the air bubbles and thus a change in the quantity of the liquid sent to said analytical portion T is detected and used to automatically control the pump speed so as to always maintain the flow at a set value in a feedback control arrangement, which works because the quantity of the liquid sent to the analytical portion T from the passage-change over valve mechanism V is closely related to the change in speed of movement of the air bubbles added to the liquid and flowing together with the liquid, and indeed there seems to be a substantially linear relation. The quantity of liquid supplied to the analytical portion T can thus always be maintained at the set value with high accuracy and for a long time even though some manufacturing error exists in the liquid-supplying tube used for the peristaltic pump P or there is a change in the property and state and characteristic of the liquid supply valve with the passage of time. Also, since, as described hereinbefore, the change of flow rate is detected by the air bubble speed-detecting means X, the detection can be carried out with remarkably high accuracy using a remarkably simple mechanism utilizing only one or two air bubble detectors, such as a conductivity meter, whereby the above described automatic control of the flow rate can be accurately carried out.

In said air bubble moving speed-detecting means X, there can be used one air bubble detector 2 constituted by, for example, a conductivity meter positioned midway in a liquid-passage 1 from the air bubble-adding mechanism R to the analytical portion T, as shown in FIG. 2, so that the speed of movement of the air bubbles can be determined by said controller Z on the basis of the elapsed time from the time the air bubble is added by the air bubble-adding mechanism R as indicated to the controller Z to the time when the air bubble is detected by said air bubble detector 2. Alternatively, as shown in FIG. 3, two air bubble detectors 2A and 2B can be provided at two positions spaced a predetermined distance along the liquid-passage 1 from the air bubble-adding mechanism R to the analytical portion T so that the speed of movement of the air bubbles can be determined by said controller Z on the basis of the elapsed time the time when an air bubble is detected by the upstream air bubble detector 2A to the time when the air bubble is detected by the downstream air bubble detector 2B.

DESCRIPTION OF THE PREFERRED EMBODIMENT

A preferred embodiment of the present invention will be described with reference to FIG. 4 and FIG. 5.

Figure 4:
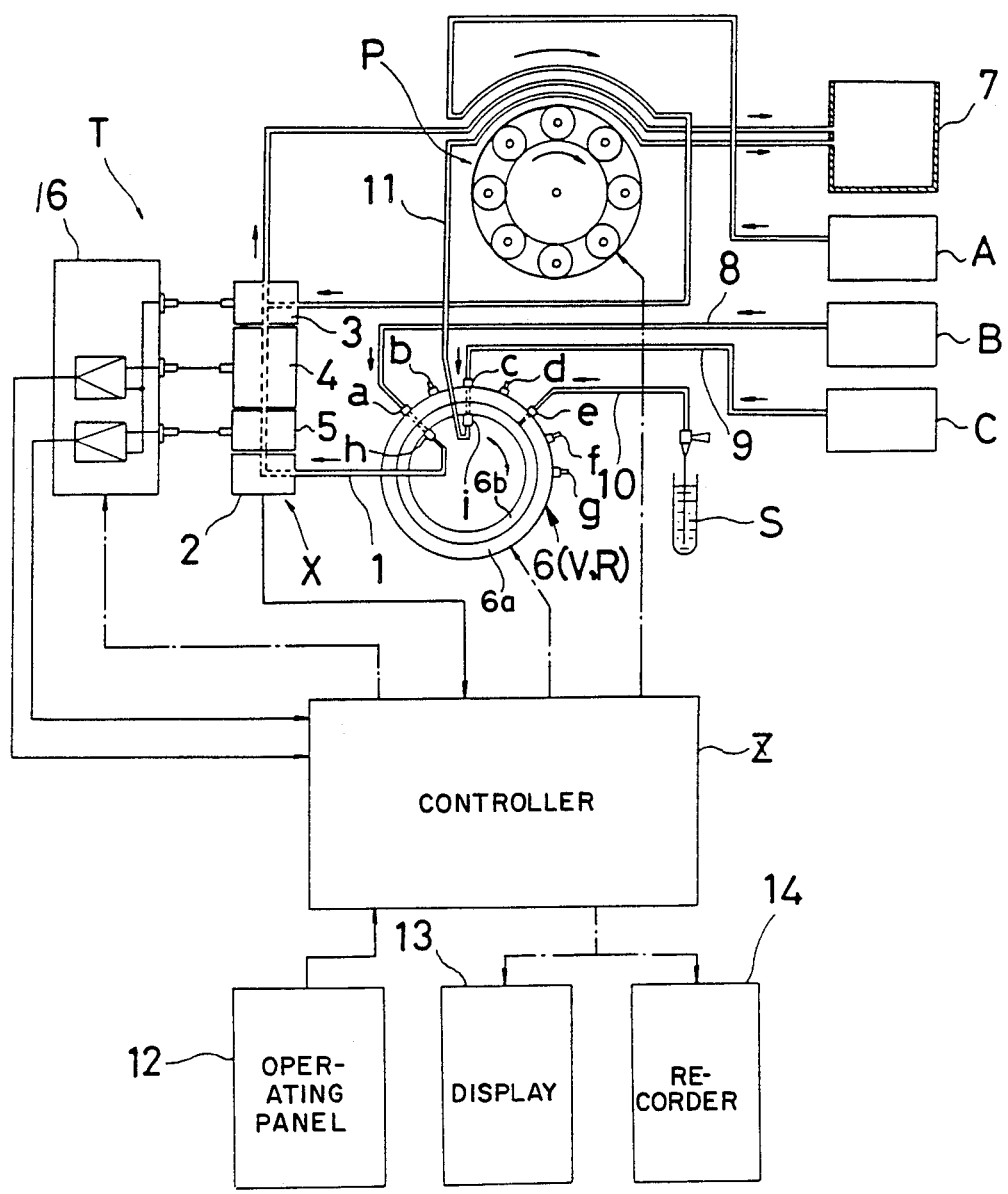
FIG. 4 is a general block of a preferred embodiment of an analyzer according to the present invention.

Referring to FIG. 4 showing the general construction of a whole apparatus, T designates an analytical portion composed of a reference electrode 3, a $Na^+$ concentration-measuring electrode or a pH-measuring electrode 4, a $K^+$, $Ca^{++}$ and the like concentration-measuring electrode 5, and a preamplifier 16 for said electrodes.

P designates a peristaltic pump, sometimes called a tubing pump, for positively pumping an internal solution A to the reference electrode, and drawing a span-calibrating solution B, a zero-calibrating solution C, and a sample solution S or the like to said analytical portion T by a suction force on tubes downstream of said analytical portion T, the desired solution being chosen by a rotary type change over valve 6, which will be described later. Pump P discharges used liquid into a waste tank 7.

The rotary type change-over valve 6 comprises a passage-change over valve mechanism V for selectively supplying said analytical portion T with various kinds of solution B, C and S drawn through valve 6 by said peristaltic pump P, and an air bubble-adding mechanism R for adding air bubbles to the liquid sent to said analytical portion T from the passage-change over valve mechanism V when the passages of the passage-changing over valve mechanism V are changed over. The valve V and mechanism R are constructed in one integrated member. Said rotary type changing-over valve 6 has inlet passages 8, 9 and 10 for said span-calibrating solution B, said zero-calibrating solution C and said sample solution S connected to inlet ports a, c and e on one member 6a of the rotary valve, the remaining inlet ports b, d, f and g being air inlet ports on said one member opening the air or an inert gas supply. A liquid-supplying passage 1 for supplying said analytical portion T with the selected liquid is connected to one outlet port h of outlet ports h and i on the other member 6b of the rotary valve and a by-pass passage 11 is connected to the other outlet port i. These outlet ports h and i are spaced a distance equal to the spacing of two inlet ports, so that they are selectively connected to inlet ports a and c, b and d, c and e etc. by rotating one of the members 6a relative to the other member 6b in a normal direction or a reverse direction. When the members are relatively rotated so that the inlet ports a, c or e, to which said inlet passages 8, 9, 10 for the span-calibrating solution B, the zero-calibrating solution and the sample solution S, are connected to the outlet ports h and i, the outlet ports move past said air inlet ports b, d, f which are alternately arranged with inlet ports a, c and e, as shown in FIG. 4, and are temporarily connected thereto so that air bubbles are automatically added to passage 1 every time a passage-changing rotation of valve 6 is carried out, either the normal rotation or the reverse rotation.

A liquid/air bubble detector 2 composed of, for example, a conductivity meter is provided at a position close to the down-stream end of the liquid-supplying passage 1 extending from said rotary type changing-over valve 6 to said analytical portion T. Said liquid/air bubble detector 2 is a constituent element of the air bubble speed-detecting means X and supplies a signal indicating detection of an air bubble to a controller Z.

Said controller Z is operable to control the change-over operation of said rotary type change-over valve 6 and the detecting operation in said analytical portion T in response to a liquid-detecting signal from said liquid-/air bubble detector 2. Also, said controller Z is operable to detect the speed of movement of the air bubbles and from this to determine the flow rate of the liquid on the basis of the amount of time from the time when the change-over operation of said rotary type change-over valve 6 took place, i.e. the time when air bubbles were added, to the time when an air bubble-detecting signal from said liquid/air bubble detector 2 was received, to compare the flow rate with a predetermined flow rate, and to control the speed of rotation of said peristaltic pump P by a feedback control on the basis of the determined amount of time, thereby automatically maintaining the flow rate of the liquid to said analytical portion T at the predetermined value.

An operative panel 12 is provided for inputting the predetermined value of the flow rate and the change over of the valve 6 to said controller Z. The output of the analytical portion is displayed on a displaying apparatus 13 and recorded on a recording means 14.

The control of the speed of rotation of the peristaltic pump P by said controller Z used in this embodiment will be described in further detail.

Figure 5:
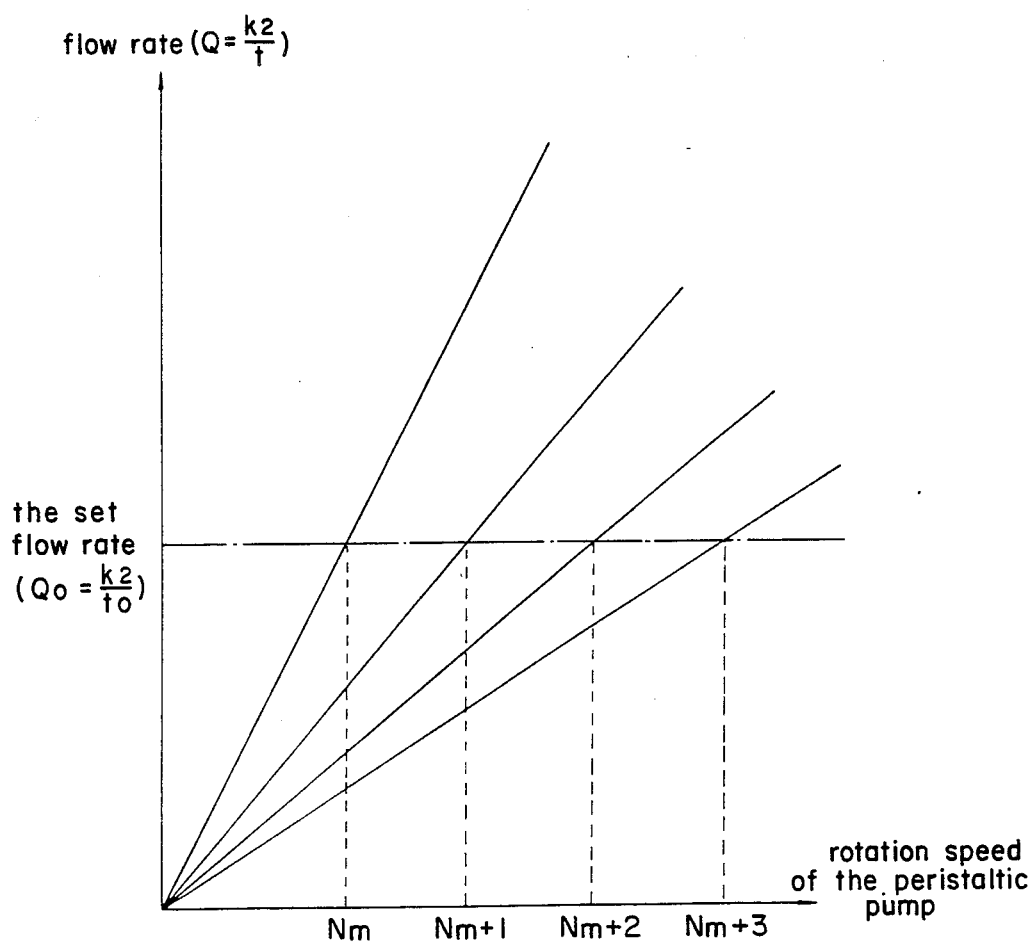
FIG. 5 is a graph for illustrating a control mode of the apparatus of FIG. 4.

Although the relation between the flow rate Q of the liquid sent to the analytical portion T through said liquid-supplying passage 1 and the speed of rotation N of said peristaltic pump P can be expressed in the general form of $Q = k_1 \cdot N$, this relation can change due to the deterioration and the like of the tube used in the peristaltic pump P with the passage of time, as illustrated in FIG. 5. On the other hand, since the air bubble-movement time t from the time when said rotary type changing-over valve 6 was changed over to add air bubbles to the liquid-supplying passage 1 to the time when the air bubbles is detected by said liquid/air bubble detector 2, is inversely proportional to said flow rate Q, the equation $Q = k_2/t$ holds good, whereby the relation of $N \cdot t = k_2/k_1$ holds good. Consequently, in order to maintain a desired flow rate $Q_o$ an initial air bubble-movement time to for the desired flow rate $Q_o$ is set and the initial speed of rotation $N_o$ of the peristaltic pump P for that time is set. Then the rotation speed N of the peristaltic pump P and the air bubble-moving time t are periodically detected and the speed of rotation N of the peristaltic pump P is controlled so as to approach a value calculated by the following asymptotic equation:

$$N_m = N_{m-1} \cdot t_{m-1}/t_o$$

(m; a whole number)

As is obvious from the above detailed description, with a flow through type liquid analyzer according to the present invention, since a change in the velocity of flow of liquid sent to an analytical portion and the consequently change in quantity is detected by effectively utilizing air bubbles, which originally exist within the liquid in a liquid analyzer of the type, in short, detecting a change in the speed of movement of air bubbles, the quantity of the liquid sent to the analytical portion is automatically controlled so as to always be maintained at a set value by a feedback control on the basis of the detected result, so that the amount of liquid supplied to the analytical portion can always be maintained at the set value with high accuracy and for a long time. This is accomplished by a comparatively simple construction even though manufacturing errors may exist to some extent in the liquid-supply tube used in the peristaltic pump or the properties of the liquid-supply tube change with the passage of time. Thus, measurement errors due to variations in the flow rate can be greatly reduced. In addition, various superior effects can be obtained, for example, the measuring time can be made constant and the set flow rate can be optionally changed very easily.

What is claimed is:

1. A flow through type liquid analyzer comprising:
   an analytical portion;
   a peristaltic pump connected to said analytical portion for supplying various kinds of liquids to said analytical portion;
   a passage-change over valve mechanism for controlling the kinds of liquid supplied to said analytical portion;
   an air bubble adding mechanism for adding air bubbles to the liquid sent to said analytical portion from said passage-change over valve mechanism;
   means for detecting the movement of the air bubbles from said air bubble adding mechanism to said analytical portion; and
   a controller connected to said detecting means and to said pump for determining the flow rate of the liquid being sent to said analytical portion from said detected movement means, comparing this flow rate with a predetermined desired constant flow rate, and when a changed flow rate is detected, controlling the speed of rotation of said pump in response to the changed flow rate in a manner for automatically maintaining the flow rate of the liquid sent to said analytical portion at said predetermined desired constant flow rate.

2. A liquid analyzer as claimed in claim 1 in which said change-over valve mechanism and said air bubbles adding mechanism comprise a rotary changeover valve having means for adding air bubbles each time said rotary changeover valve is rotated for changing over the kind of liquid supplied to said analytical portion.

3. A liquid analyzer as claimed in claim 1 in which said passage-change over valve mechanism has a connection to said analytical portion, said connection having a downstream end, and said detecting means comprises a single air bubble detector at the downstream end of the connection between said passage-change over valve mechanism and said analytical portion, and said controller comprises means for determining the length of time from the time of actuation of passage-change over valve mechanism to the time of detection of an air bubble.

4. A liquid analyzer as claimed in claim 1 in which said passage-change over valve mechanism has a connection to said analytical portion, and said detecting means comprises a pair of air bubble detectors spaced along the connection between said passage-change over valve mechanism and said analytical portion, and said controller comprises means for determining the length of time between the detection of an air bubble by the successive air bubble detectors.

* * * * *